(12) United States Patent
Weill et al.

(10) Patent No.: US 7,776,157 B2
(45) Date of Patent: Aug. 17, 2010

(54) SIMPLIFIED DEVICE FOR CLEANING AN OBJECT

(75) Inventors: David Weill, Chemin Champ-David, 1268 Begnins (CH); Claude Schindler, Geneva (CH)

(73) Assignee: David Weill, Begnins (CH)

( * ) Notice: Subject to any disclaimer, the term of this patent is extended or adjusted under 35 U.S.C. 154(b) by 639 days.

(21) Appl. No.: 11/629,338

(22) PCT Filed: Jun. 9, 2005

(86) PCT No.: PCT/IB2005/001608
§ 371 (c)(1),
(2), (4) Date: Dec. 11, 2006

(87) PCT Pub. No.: WO2005/120735
PCT Pub. Date: Dec. 22, 2005

(65) Prior Publication Data
US 2008/0047590 A1    Feb. 28, 2008

(30) Foreign Application Priority Data
Jun. 11, 2004    (FR) .................................... 04 06330

(51) Int. Cl.
*B08B 3/04*    (2006.01)
*B08B 11/02*    (2006.01)
(52) U.S. Cl. .................. 134/21; 134/34; 134/58 R; 134/201
(58) Field of Classification Search .................. 134/21, 134/58 R, 34
See application file for complete search history.

(56) References Cited

U.S. PATENT DOCUMENTS

| | | | |
|---|---|---|---|
| 6,824,751 B2 | 11/2004 | Rossell | |
| 2002/0018735 A1 * | 2/2002 | Rossell | 422/128 |

FOREIGN PATENT DOCUMENTS

| | | | |
|---|---|---|---|
| CA | 2192700 | * | 12/1995 |
| EP | 0 521 119 B | | 5/1996 |
| WO | WO 92/12685 | | 8/1992 |
| WO | WO 95/35069 | | 12/1995 |
| WO | WO 00/45859 | | 8/2000 |

* cited by examiner

*Primary Examiner*—Michael Kornakov
*Assistant Examiner*—Natasha Campbell
(74) *Attorney, Agent, or Firm*—Frommer Lawrence & Haug LLP (57) ABSTRACT

A cleaning device comprising an enclosure, a cover allowing it to be opened in order to place an object to be cleaned within the enclosure, a supply of cleaning fluid, the enclosure comprising a piston that can move thanks to a motor, a geometry allowing a contact with an external fluid reservoir when the piston occupies a certain position within the enclosure in order to generate a sudden release of pressure, the device comprising an outlet valve remaining closed when the piston increases the volume of the enclosure so as to cause the pressure reduction within the enclosures.

10 Claims, 6 Drawing Sheets

SIMPLIFIED DEVICE FOR CLEANING AN OBJECT

This application is a 371 of PCT/IB2005/001608 filed on Jun. 9, 2005, published on Dec. 22, 2005 under publication number WO 2005/120735 A1 which claims priority benefits from French Patent Application Number 04/06330 filed Jun. 11, 2004.

The invention relates to a method and a device for cleaning a delicate object. It is particularly suitable for cleaning objects requiring particular hygiene conditions, for example, contact lenses.

DESCRIPTION OF THE PRIOR ART

One solution for cleaning a contact lens is described in document EP0521119. This solution is based on a device having a chamber that can accommodate a contact lens. This device is in contact, on the one hand, with a pump that creates a vacuum and on the other hand with a device having a piston, which has the function of introducing a pressurized cleaning fluid into the chamber. This device operates on the basis of the cavitation phenomena, of which the high energy involved makes it possible to reach a high level of cleaning. However, such a solution requires two controlled pumping systems, relatively long ducts, many connections, depends on the inertia of the components in motion, the inertia of the columns of liquids in motion and is subjected to the various damping factors associated with the various components such as the ducts in the context of the pressure variations. This solution relies therefore on a complex mechanism posing problems of reliability. In addition, the energy consumed is considerable and this solution causes a considerable consumption of cleaning liquid. Finally, it generates cavitation phenomena that are always accompanied by often undesirable violent effects.

Another solution for cleaning a contact lens using cavitation is described in document EP1146914. It consists in the creation of a low pressure by a device that is periodically placed in contact with the enclosure containing the lens to be cleaned, in alternation with a setting at atmospheric pressure. This solution is based on a rotor rotated by a motor and containing several internal ducts to connect the various pressure sources to the cavity of the closed enclosure. This device has many disadvantages like those mentioned previously, to which the fact of using the rotor is added: specifically, this device requires particular connections between the ducts, causes losses of energy and wear by friction, problems of sealing and hygiene because the liquid passes through the rotor.

SUMMARY OF THE INVENTION

A first object of the invention is to propose a cleaning method and a cleaning device that make it possible to obtain a good result and in a short time.

A second object of the invention consists in proposing a simple method and device, of little bulk and low cost.

The concept of the invention consists in subjecting the enclosure containing the object to be cleaned, to cycles of sudden pressure releases, causing a particular motion of fluid, gaseous, liquid and even pasty, within the enclosure, which has the effect of cleaning the enclosure.

More precisely, the cleaning device according to the invention comprises an enclosure, a cover, allowing it to be opened in order to place an object to be cleaned, such as a contact lens, within the enclosure, a supply of cleaning fluid, the enclosure comprising a piston that can move thanks to a motor, a geometry allowing contact with an external fluid reservoir when the piston occupies a certain position within the enclosure in order to generate a sudden release of pressure, the device comprising an outlet valve remaining closed when the piston increases the volume of the enclosure so as to cause the pressure reduction within the enclosure.

The device may also comprise a spring opposing the motor and allowing the movement of the piston in a first direction, the motor causing the movement of the piston in a contrary direction.

The outlet of the valve may be connected via a duct to a fluid reservoir containing the cleaning liquid so as to form a closed circuit for the fluid.

The particular geometry of the enclosure may consist of a hole, a groove or an enlargement in cross section in order to allow contact with the fluid reservoir and/or with the external air when the piston occupies a certain position within the enclosure so as to generate the sudden release of pressure.

The device may include a means of concentrating the waves in that region of the enclosure where the object to be cleaned is placed.

The invention also relates to a method for cleaning an object positioned in an enclosure of a device as described above, comprising a repetition of the following steps:

a motor pushes a piston in the direction of reducing the volume of the enclosure, the pressure of the enclosure remaining constant under the effect of an open outlet valve, the motor pulls the piston in the opposite direction so as to increase the volume of the enclosure, the valve being closed, which causes the pressure reduction within the enclosure, sudden release of pressure within the enclosure by placing the enclosure in contact with an external fluid when the piston reaches a particular geometry of the enclosure.

This method may include, in parallel with the previous steps, a step of supplying the enclosure with cleaning fluid.

DESCRIPTION OF THE DRAWINGS

These objects, features and advantages and others of the present invention will be explained in detail in the following description of particular embodiments given on a nonlimiting basis in relation to the appended figures amongst which.

DESCRIPTION OF THE PREFERRED EMBODIMENTS

Figure 1:
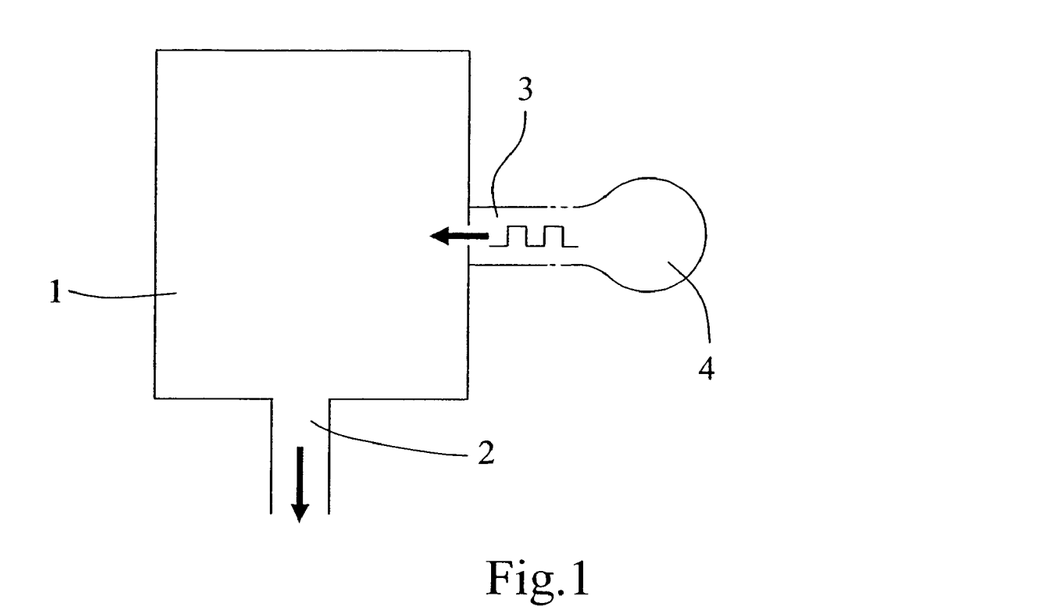
FIG. 1 represents a schematic view illustrating the concept of the invention.
Figure 2:
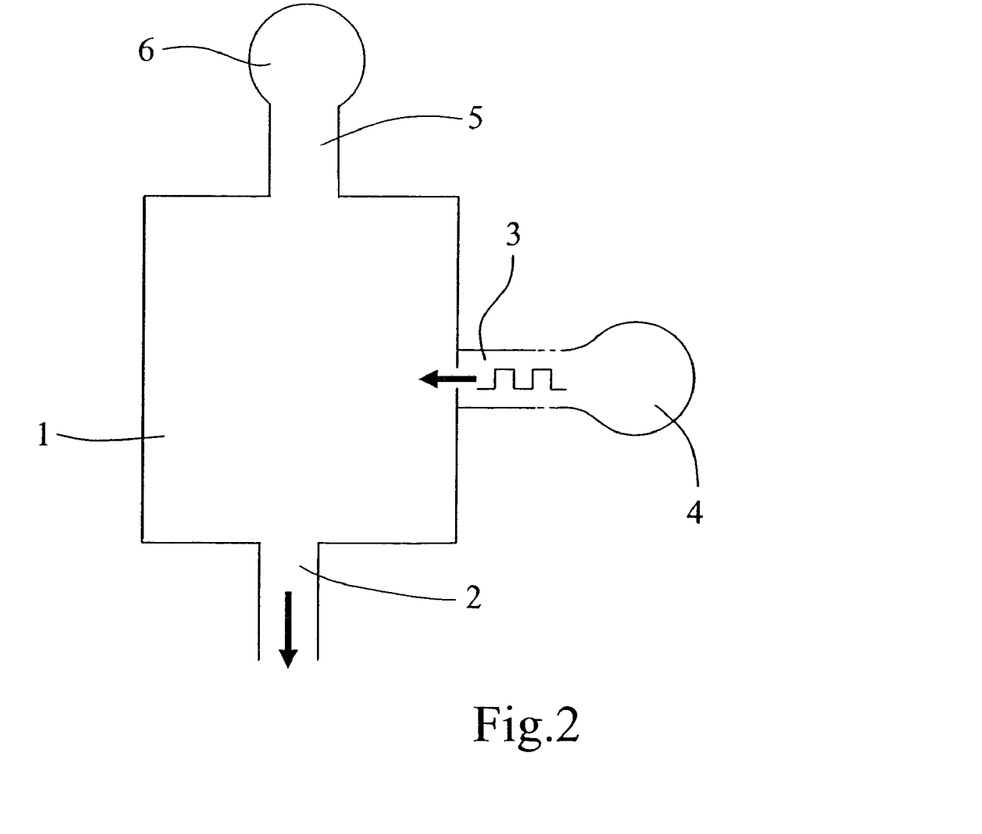
FIG. 2 represents a schematic view of a variant of a device according to the concept of the invention.
Figure 3:
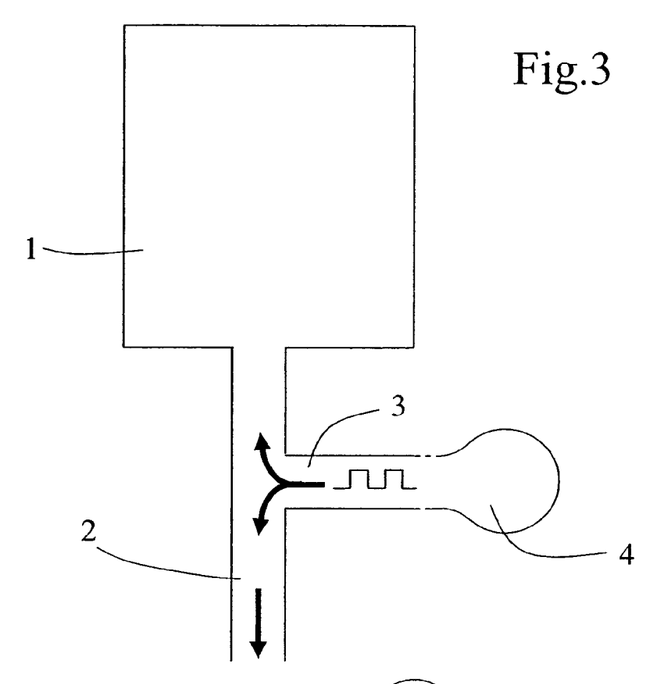
FIG. 3 represents a variant of the diagram of FIG. 1.

FIGS. 1 to 3 represent schematic devices illustrating the concept of the invention.

FIG. 1 illustrates a closed cavity 1 within which an object to be cleaned is placed. The device according to the invention comprises a pressure reduction means 2 connected to the cavity via a first opening, this means being a pump in this embodiment, a means of sudden pressure release 3 connected to the enclosure 1 via a second opening, this means being a valve-type release device in this embodiment and this means being connected to a reservoir containing a fluid 4, air at atmospheric pressure in this embodiment.

The cleaning method of the invention, applied with the aid of the foregoing device, comprises the following essential steps:

reduction of the pressure inside the enclosure 1 with the aid of the suction pump 2 which sucks out the air present in the enclosure;

below a certain threshold pressure, sudden release caused by the valve 3, which consists in the sudden inrush of the air 4 into the enclosure and causes the sudden pressure increase inside the enclosure.

The foregoing steps are repeated cyclically.

The pressure reduction means 2 may be of a mechanical type such as a pump, of the hydraulic type, such as a turbine, of the electromechanical type, such as a vibration pump whose operating cycle is sufficiently high to be considered continuous. It operates in a continuous or virtually continuous manner so that it causes a virtually permanent flow of air within the enclosure.

The release device 3 has the function of causing a sudden pressure increase, and may consist in a simple device suddenly placing the enclosure at low pressure in contact with the outside at constant pressure, such as the air at atmospheric pressure for example. It may consist in a simple mechanical device consisting of a ball blocking off an opening of the enclosure and connected to a spring, this ball being able to be moved so as to release the opening of the enclosure when the pressure difference between the inside and the outside of the enclosure reaches a sufficient value to oppose the force of the spring. This device may also be based on the constant elasticity of a material that makes it possible to open a valve when the pressure reduction exceeds a certain threshold. This phenomenon causes a sudden change in the virtually permanent flow.

The combination and repetition of the two foregoing effects make it possible to create a circulation of air marked by violent movements inside the enclosure which makes it possible to obtain a better cleaning than with a simple flow.

This device may also be used with any fluid 4. Note that in the case of a liquid such as water, by nature incompressible, such a device remains effective by the fact that there always remain at least a few air bubbles within the enclosure, a phenomenon due to the imperfect geometry of the walls of the enclosure, to the possible presence of solid or liquid contaminants, and possible imperfect sealing of the enclosure at the openings for example, which allows the device to produce the pressure cycle described hereinabove. According to the concept of the invention, the extreme conditions of cavitation are not sought and are not necessary, unlike the prior art. However, the invention remains compatible with these extreme conditions and nothing would prevent the device from operating in such conditions if certain applications required it.

FIG. 2 represents a schematic view of a variant embodiment. In this variant, the device includes additionally a means 5 of supplying a fluid 6, water in this embodiment, through a third opening in the enclosure 1. The supply means may be a simple duct connected to a water reservoir at a certain pressure, advantageously high and constant.

This device makes it possible to carry out the following steps:

reduction of the air pressure inside the enclosure 1 with the aid of the suction pump 2 which sucks out the air present in the enclosure;

in parallel, filling of the enclosure with the water originating from the supply means 5, this filling being promoted by the pressure of the water at the inlet and by the suction via the means 2;

below a certain threshold pressure, sudden release caused by the valve 3, which consists in the sudden inrush of the air 4 into the enclosure and causes the sudden pressure increase inside the enclosure.

Note that this device makes it possible to obtain the following effects:

the release of air inside the enclosure creates an impact inside the enclosure, that is transmitted into the volume of the enclosure by the water due to its virtually incompressible character;

without any particular priming method, the enclosure finishes by being filled with water, this filling being better than in the case of a simple supply of water. Specifically, this device makes it possible to reach any corners of the enclosure, under the effect of the sudden releases;

nevertheless, there always remain a few gas bubbles which allow the suction then release mechanism to continue operating even when the enclosure is almost entirely full of water. These air bubbles are of very small size and often invisible to the naked eye at atmospheric pressure. They may move at random with the sudden convection movements generated by the releases and they have a volume which increases with the pressure reduction, this volume variation also being able to be an additional source of convection movement in the liquid. Thanks to these phenomena, the gas bubbles actively participate in the cleaning of the surfaces;

the cleaning effect within the enclosure is very effective.

Finally, this device makes it possible to combine the action of two complementary fluids, the air which allows a mechanism of pressure reduction then sudden release, and the water, with an addition of liquid cleaning product, which has a more effective cleaning effect than the air alone, and participates effectively in the transmission of the shock waves. Naturally, any other combination of fluids, liquid, gaseous and even pasty, is possible, as is the use of a liquid comprising solid particles in suspension.

This device and method therefore make it possible to obtain improved cleaning.

FIG. 3 represents schematically a variant of the device of FIG. 1, which has the advantage of requiring only a single opening in the enclosure 1 to use the functions of pressure reduction and sudden pressure release. Specifically, in this case, the pressure release device 3, in the form of a valve, is connected to an opening of the outlet duct of the pressure reduction mechanism.

Figure 4:
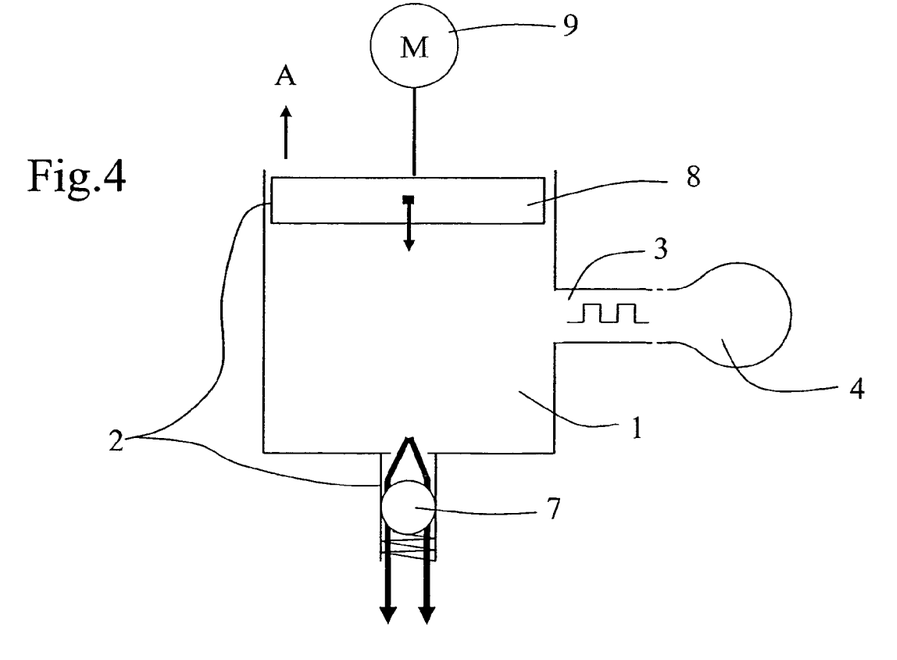
FIG. 4 represents an embodiment with piston.

FIG. 4 represents schematically a variant embodiment of the mechanism of FIG. 1. This device comprises an outlet valve 7 connected to the enclosure 1 via a first opening, a release device 3 as described previously. The enclosure comprises an open part closed by a piston 8, this piston being able to be set in motion in the direction of the arrow A or in the contrary direction with the aid of a motor 9.

This device operates as follows:

according to a first phase, the motor 9 pushes the piston 8 in the direction contrary to the arrow A, which causes the discharge of the air from the enclosure via the valve 7, the pressure of the enclosure remaining constant;

then the motor 9 sets the piston in motion in the direction of the arrow A, which has the effect of reducing the pressure of the enclosure, the valve 7 remaining closed in this phase;

beyond a certain value of this pressure, the device 3 causes a sudden release within the enclosure, which causes a sudden increase in the pressure and the filling of the enclosure with air.

It is therefore evident that this device makes it possible to use the method of the device of FIG. 1, described hereinabove.

In this embodiment, the pressure reduction method consists in an outlet valve 7, a piston 8 and a motor 9.

Figure 5A:
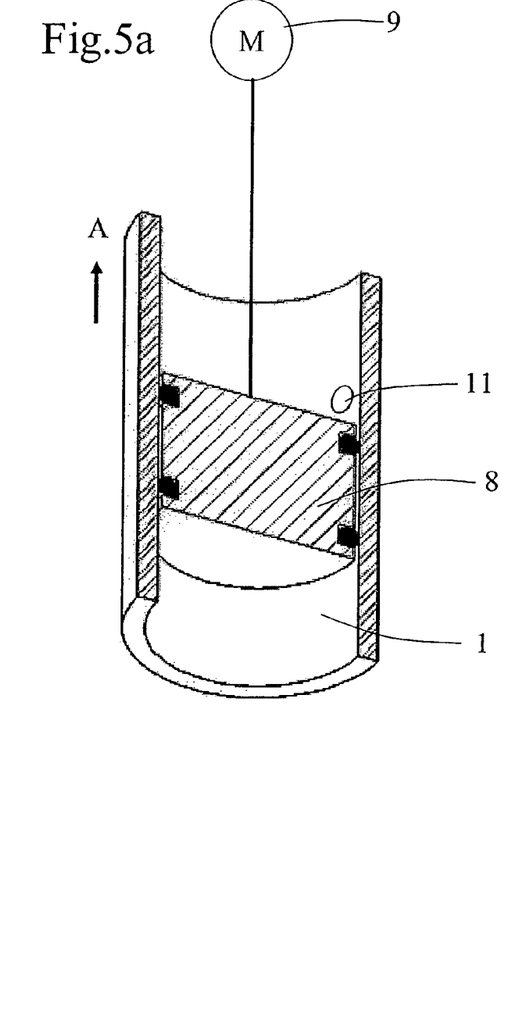
FIGS. 5a to 5c are variant embodiments of the means of sudden release of pressure.
Figure 5B:
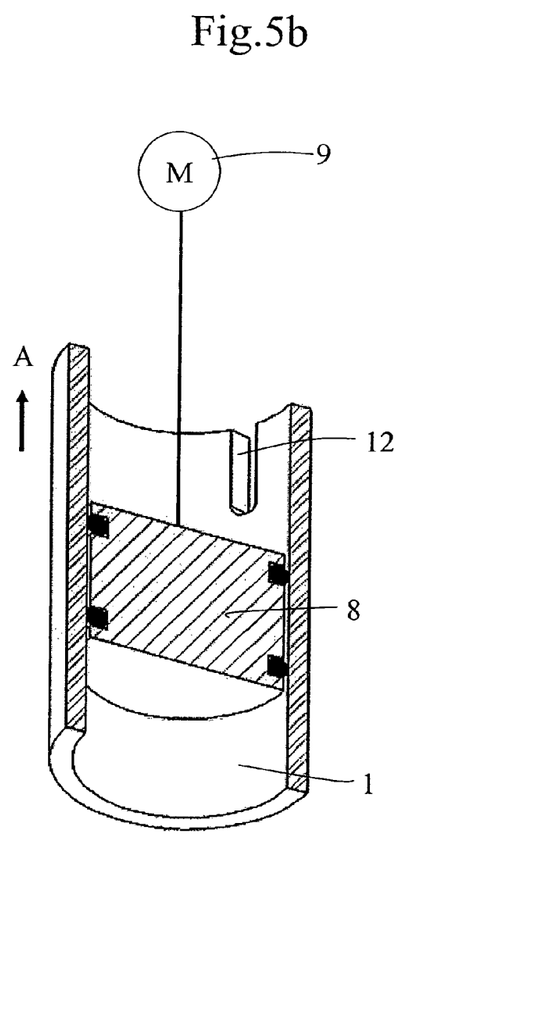
Figure 5C:
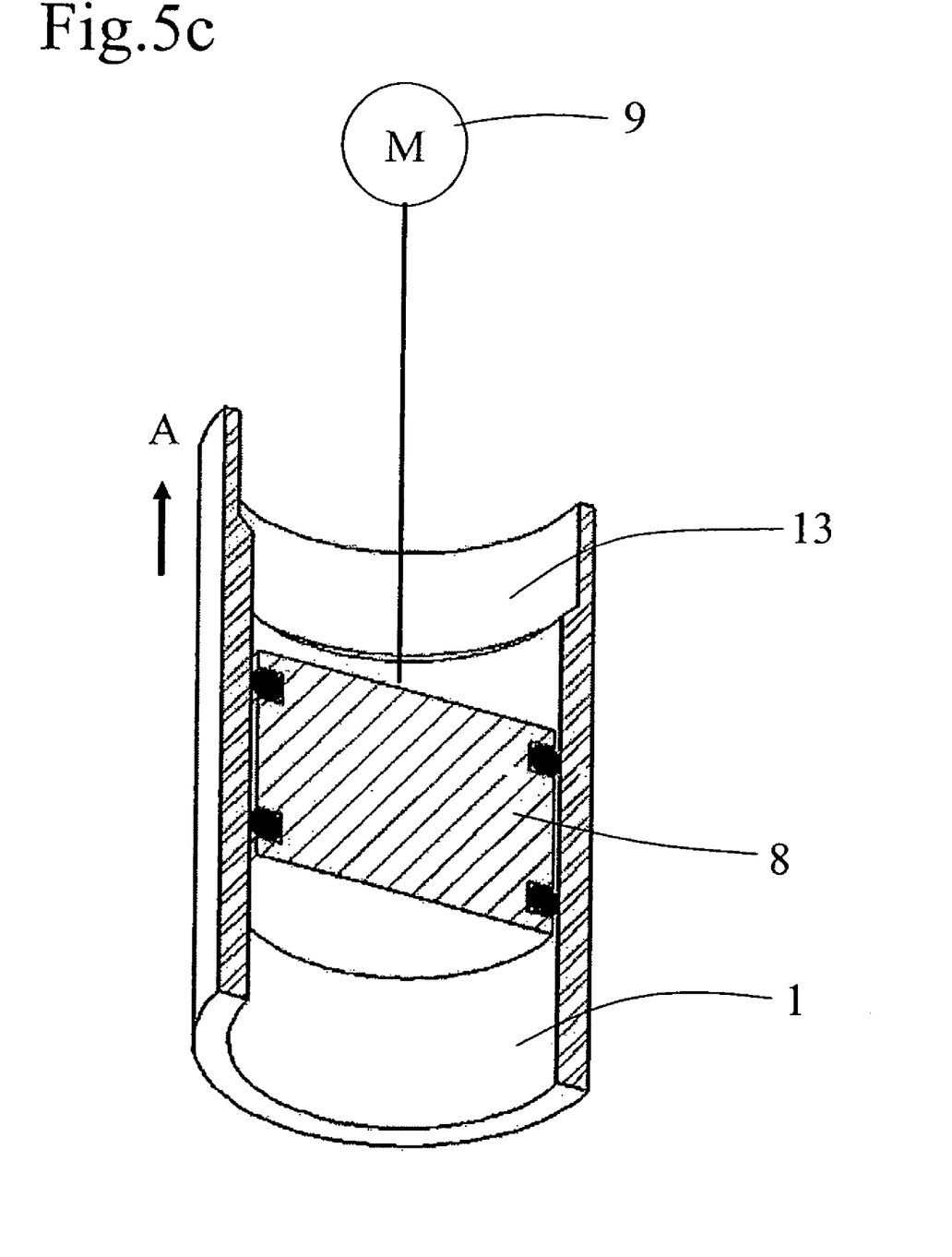

FIGS. 5a to 5c represent variant embodiments of the device of FIG. 4, with simplified sudden pressure release devices.

Specifically, FIG. 5a represents in section a cylindrical enclosure in which a hole 11 is made in its wall, allowing a contact with the air at atmospheric pressure. In this device, when the piston, which moves in the direction of the arrow A causing the enclosure 1 to be placed at low pressure, reaches a position in which it is beyond the hole 11, the enclosure at low pressure is suddenly placed in contact with the outside air at atmospheric pressure, which causes the sudden release effect. Thus, the sudden pressure release device is filled by the combination of the piston 8 and the hole 11 in this device.

As a comment, this device combines the two functions of pressure reduction 2 and of sudden release 3 by means of the piston 8, which makes it a controlled system, unlike the preceding devices in which the two means operated independently.

The device of FIG. 5b represents a variant in which the hole 11 is replaced by a groove 12.

The device of FIG. 5c represents a variant in which the hole 11 is replaced by an enlargement 13 of the cross section of the enclosure, which allows the air to pass at the sides, via the space that lies between the wall of the enlarged enclosure and the piston.

Figure 6:
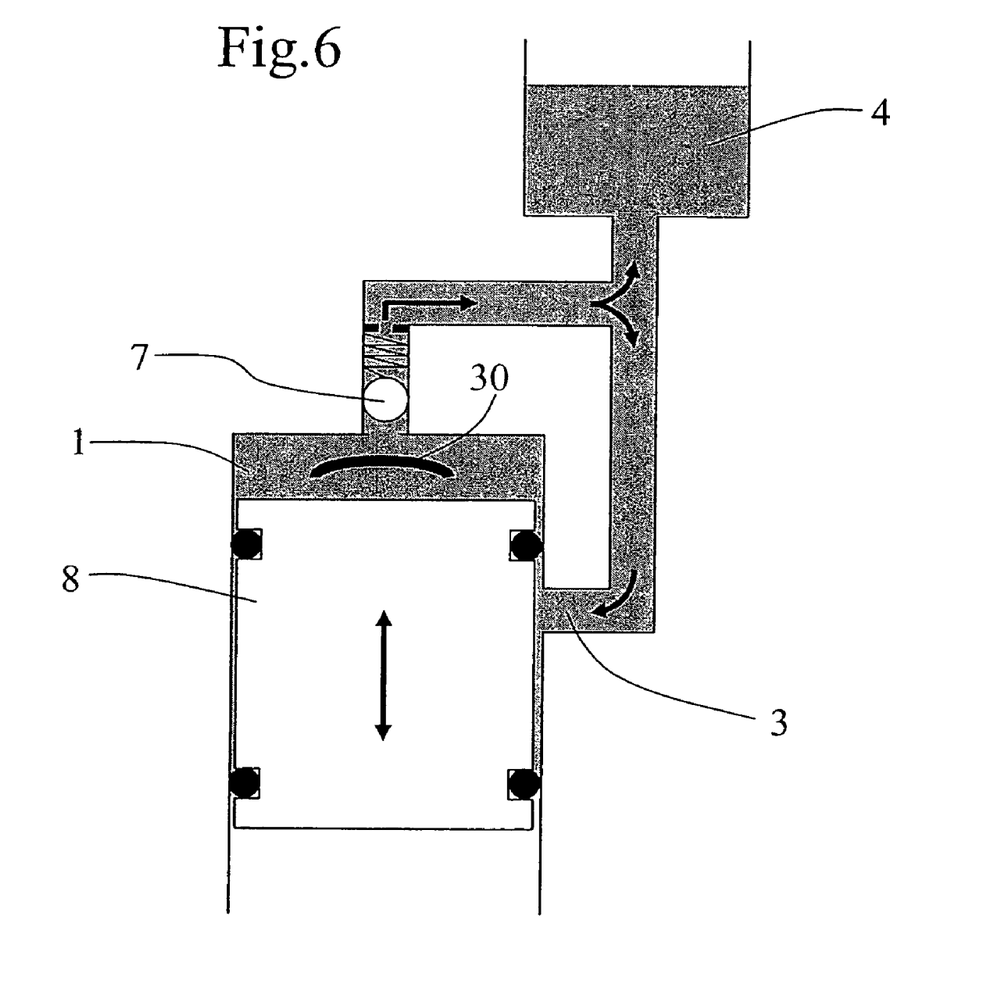
FIG. 6 is a device according to the invention for cleaning contact lenses.

FIG. 6 represents a device based on the diagram shown in FIG. 4 in an application for cleaning a contact lens 30. This device contains a piston 8 and a valve 7, the possible structures and functions of which have been explained above. It also contains a release device 3 connected to a reservoir 4 containing a fluid-cleaning water in this particular application. According to this device, a duct is placed at the outlet of the valve 7 and is connected to the reservoir 4 of the expansion tank type, so as to obtain a closed water circulation circuit. The object to be cleaned, such as a contact lens 30, may be placed in the enclosure 1.

This device makes it possible to clean the lenses surprisingly well. With a motor speed of 2 rpm lasting ten minutes and a cleaning liquid diluted to 50%, which is less aggressive and environmentally more friendly, the result obtained is equivalent to that obtained by immersing the lens for 24 hours.

Figure 7:
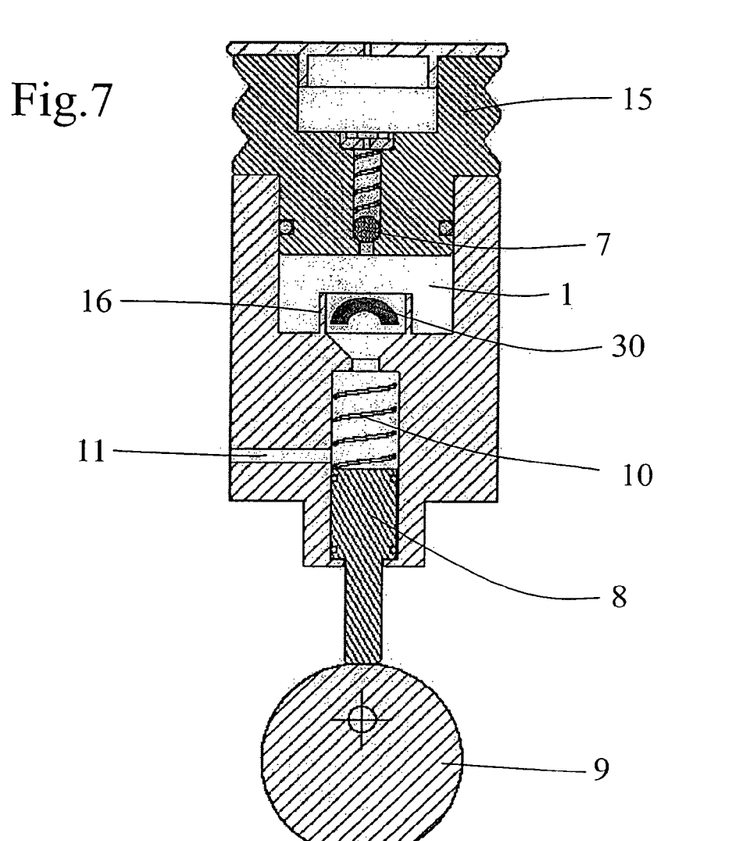
FIG. 7 is a variant embodiment of FIG. 6.

A variant of this device is represented in perspective in FIG. 7. In this variant, the release is achieved with air via an opening 11 made in the enclosure, as in the embodiment shown in FIG. 5a, and there is no longer a closed water circulation circuit. The device has a cover 15, which can be removed so as to place the contact lens in the cavity 1. The geometry of the air inlet duct and of the cavity 1 may include small internal walls 16 so as to allow the shock waves of the release to be concentrated in that region where the contact lens 30 is located, preferably near the fluid entry 4 into the enclosure 1.

As a variant, it is possible to combine the two synchronized release devices, with water and air, or with an appropriate lag in order to obtain equilibrium between sudden release and filling.

Figure 8:
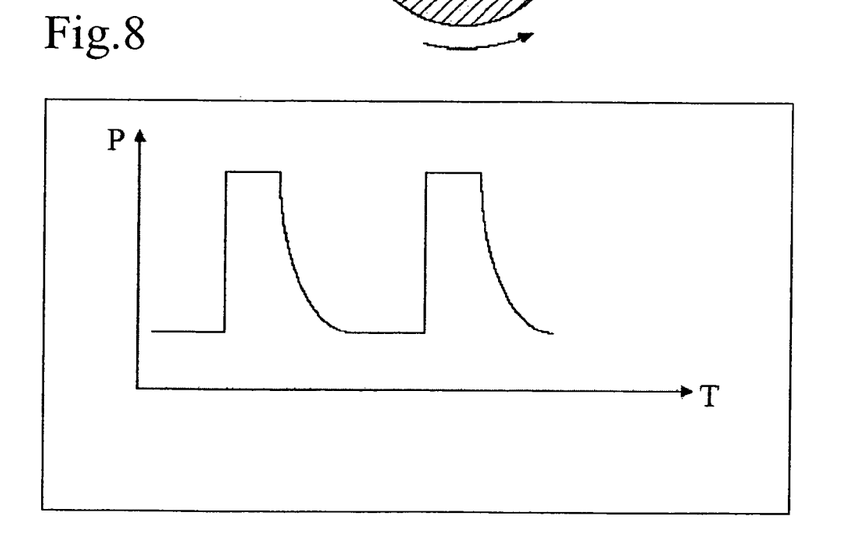
FIG. 8 represents the pressure curve as a function of the time within the device according to the invention of FIG. 7.

This device makes it possible to achieve the pressure curve shown in FIG. 8 within the cavity 1. In a first phase, during which the piston reduces the volume of the enclosure 1, the pressure remains constant and equal to atmospheric pressure. In a second phase, during which the piston increases the volume of the enclosure 1, the pressure reduces progressively and in the third phase, the pressure suddenly rises again, that is to say in a very short time, to atmospheric pressure.

Those skilled in the art will adapt the device to suit it to the objects to be cleaned.

As an additional comment, this device can function in other particular conditions in which there is a change of state of a fluid, in which there are cavitation phenomena. It remains compatible with the addition of complementary components such as pressure sensors, devices such as a transducer in contact with the fluid or submerged in the cavity in order to add complementary vibratory phenomena, of the ultrasound type for example.

The device and method of the invention finally have the following advantages:
- it makes it possible to achieve very good cleaning performance in a short time;
- it is very simple and of low cost;
- it is not very bulky; and
- it operates only with a simple motor consuming little energy.

The invention claimed is:

1. A cleaning device, comprising:
an enclosure (1),
a cover (15), allowing it to be opened in order to place an object (30) to be cleaned within the enclosure, and
a supply of cleaning fluid (4),
wherein the enclosure (1) comprises:
   a piston (8) that can move with the aid of a motor (9), and
      wherein the enclosure (1) comprises a geometry (11, 12, 13) allowing a contact with an external fluid reservoir when the piston occupies a certain position within the enclosure (1) in order to generate a sudden release of pressure,
wherein the device comprises an outlet valve remaining closed when the piston increases the volume of the enclosure so as to cause the pressure reduction within the enclosure (1), wherein when the motor (9) pushes the piston (8) within the enclosure (1) in the direction of reducing the volume of the enclosure (1), the pressure of the enclosure (1) remains constant under the effect of an open outlet valve (7), wherein when the motor (9) pulls the piston in the opposite direction so as to increase the volume of the enclosure (1), with the valve (7) being closed, the pressure reduces within the enclosure (1), and wherein there is a sudden release of pressure within the enclosure (1) by placing the enclosure (1) in contact with the external fluid when the piston (8) reaches the geometry (11; 12; 13) of the enclosure (1).

2. The device as claimed in claim 1, which also comprises a spring (10) opposing the motor (9) and allowing the movement of the piston (8) in a first direction, the motor (9) causing the movement of the piston (8) in a contrary direction.

3. The device as claimed in claim 1, which includes a duct connecting the outlet of the valve (7) to the fluid reservoir (4) containing the cleaning fluid so as to form a closed circuit for the fluid (4).

4. The device as claimed in claim 3, wherein the geometry (11, 12, 13) allows contact with the external fluid reservoir when the piston occupies a certain position within the enclosure (1) so as to generate the sudden release of pressure.

5. The device as claimed in claim 1, wherein the geometry of the enclosure (11, 12, 13) allows the enclosure to come into contact with the external air when the piston occupies a certain position within the enclosure (1) in order to generate the sudden release of pressure.

6. The device as claimed in claim 1, which includes means (16) for concentrating shock waves in that region of the enclosure where the object to be cleaned is placed.

7. A method for cleaning an object (30) positioned in an enclosure (1), which comprises a repetition of the following steps:

a motor (9) pushes a piston (8) within the enclosure (1) in the direction of reducing the volume of the enclosure (1), the pressure of the enclosure (1) remaining constant under the effect of an open outlet valve (7), the motor (9) pulls the piston in the opposite direction so as to increase the volume of the enclosure (1), the valve (7) being closed, which causes the pressure reduction within the enclosure (1), and a sudden release of pressure is created within the enclosure (1) by placing the enclosure (1) in contact with a cleaning fluid when the piston (8) reaches a geometry (11; 12; 13) of the enclosure (1).

8. The method for cleaning an object (30) as claimed in claim 7, wherein the motor (9) consists in a motor (9) operating in only one direction, the movement of the piston (8) in the other direction being implemented by a spring (10).

9. The method as claimed in claim 7, which comprises, in parallel with the preceding steps, a step of supplying the enclosure (1) with cleaning fluid.

10. The application of the device as claimed in claim 1 for cleaning a contact lens (30) positioned in the enclosure (1), which comprises a repetition of the following steps:

the motor (9) pushes the piston (8) within the enclosure (1) in the direction of reducing the volume of the enclosure (1), the pressure of the enclosure (1) remaining constant under the effect of the open outlet valve (7), the motor (9) pulls the piston in the opposite direction so as to increase the volume of the enclosure (1), the valve (7) being closed, which causes the pressure reduction within the enclosure (1), and a sudden release of pressure is created within the enclosure (1) by placing the enclosure (1) in contact with a cleaning fluid when the piston (8) reaches the geometry (11; 12; 13) of the enclosure (1).

* * * * *